(12) United States Patent
Mordaunt et al.

(10) Patent No.: US 10,179,071 B2
(45) Date of Patent: Jan. 15, 2019

(54) SYSTEM AND METHOD FOR GENERATING TREATMENT PATTERNS

(71) Applicant: Topcon Medical Laser Systems, Inc., Santa Clara, CA (US)

(72) Inventors: David Haydn Mordaunt, Los Gatos, CA (US); George Marcellino, Santa Cruz, CA (US); Michael W. Wiltberger, Santa Clara, CA (US); Justin Hendrickson, Carlisle, MA (US); Katrina Bell, Palo Alto, CA (US); Dan E. Andersen, Menlo Park, CA (US)

(73) Assignee: TOPCON MEDICAL LASER SYSTEMS, INC., Santa Clara, CA (US)

( * ) Notice: Subject to any disclaimer, the term of this patent is extended or adjusted under 35 U.S.C. 154(b) by 555 days.

(21) Appl. No.: 14/285,205

(22) Filed: May 22, 2014

(65) Prior Publication Data
US 2015/0100049 A1   Apr. 9, 2015

Related U.S. Application Data

(63) Continuation of application No. 11/523,392, filed on Sep. 18, 2006.
(Continued)

(51) Int. Cl.
*A61F 9/008* (2006.01)
*A61B 18/22* (2006.01)
*A61B 18/20* (2006.01)

(52) U.S. Cl.
CPC .......... *A61F 9/00823* (2013.01); *A61B 18/22* (2013.01); *A61F 9/008* (2013.01);
(Continued)

(58) Field of Classification Search
CPC .............................................. A61F 9/008–9/009
(Continued)

(56) References Cited

U.S. PATENT DOCUMENTS

| D222,584 S | 11/1971 | Lieberman |
| 3,621,181 A | 11/1971 | Young |

(Continued)

FOREIGN PATENT DOCUMENTS

| JP | 60-148566 A | 8/1985 |
| JP | 2004-121814 A | 4/2004 |

(Continued)

OTHER PUBLICATIONS

International Preliminary Report on Patentability received for PCT Patent Application No. PCT/US2006/036782, dated May 12, 2009, 6 pages.
(Continued)

*Primary Examiner* — Nathan J Jenness
(74) *Attorney, Agent, or Firm* — Dentons US LLP

(57) ABSTRACT

System and method for generating patterns P of aiming and treatment light on target eye tissue (e.g. the retina) of a patient's eye. The system includes light sources for treatment and aiming light, a scanner for generating patterns of spots of the generated light, a controller, and a graphic user interface that allows the user to select one of several possible spot patterns, adjust the spot density and/or spot size, and apply patterns with fixed or varied density. The patterns can be formed of interlaced sub-patterns and/or scanned without adjacent spots being consecutively formed to reduce localized heating. Partially or fully enclosed exclusion zones within the patterns protect sensitive target tissue from exposure to the light.

29 Claims, 10 Drawing Sheets

Related U.S. Application Data

(60) Provisional application No. 60/758,169, filed on Jan. 10, 2006, provisional application No. 60/718,762, filed on Sep. 19, 2005.

(52) U.S. Cl.
CPC .. *A61F 9/00821* (2013.01); *A61B 2018/2025* (2013.01); *A61B 2018/20359* (2017.05); *A61B 2018/2266* (2013.01); *A61B 2018/2272* (2013.01); *A61F 2009/00863* (2013.01); *A61F 2009/00878* (2013.01); *A61F 2009/00897* (2013.01)

(58) Field of Classification Search
USPC ................................ 606/4–6; 607/88–95
See application file for complete search history.

(56) References Cited

U.S. PATENT DOCUMENTS

| | | |
|---|---|---|
| 3,703,176 A | 11/1972 | Vassiliadis et al. |
| D254,933 S | 5/1980 | Muller |
| 4,653,495 A | 3/1987 | Nanaumi |
| D295,556 S | 5/1988 | Speaker |
| D299,745 S | 2/1989 | Sasaki et al. |
| 4,884,884 A | 12/1989 | Reis |
| 4,907,586 A | 3/1990 | Bille et al. |
| 4,917,486 A | 4/1990 | Raven et al. |
| 5,391,165 A | 2/1995 | Fountain et al. |
| 5,424,788 A | 6/1995 | Satake et al. |
| 5,425,729 A | 6/1995 | Ishida et al. |
| D360,465 S | 7/1995 | Niven |
| 5,480,396 A | 1/1996 | Simon et al. |
| 5,488,443 A | 1/1996 | Ota et al. |
| D367,568 S | 3/1996 | Strayer |
| 5,514,127 A | 5/1996 | Shanks |
| 5,543,866 A | 8/1996 | Van de Velde |
| 5,568,208 A | 10/1996 | Van de Velde |
| 5,599,340 A | 2/1997 | Simon et al. |
| 5,743,902 A | 4/1998 | Trost |
| 5,795,351 A | 8/1998 | Clapham |
| 5,892,569 A | 4/1999 | Van de Velde |
| 5,906,609 A | 5/1999 | Assa et al. |
| D410,661 S | 6/1999 | Wolf |
| 5,921,981 A | 7/1999 | Bahmanyar et al. |
| 5,943,117 A | 8/1999 | Van de Velde |
| 5,957,915 A | 9/1999 | Trost |
| 5,971,978 A | 10/1999 | Mukai |
| 6,047,431 A | 4/2000 | Canonica |
| 6,090,100 A | 7/2000 | Hohla |
| 6,099,522 A | 8/2000 | Knopp et al. |
| 6,132,424 A * | 10/2000 | Tang ................... A61F 9/008 606/10 |
| 6,149,643 A | 11/2000 | Herekar et al. |
| 6,149,644 A | 11/2000 | Xie |
| D435,658 S | 12/2000 | Lobel et al. |
| 6,186,628 B1 | 2/2001 | Van de Velde |
| 6,210,401 B1 | 4/2001 | Lai |
| 6,231,566 B1 * | 5/2001 | Lai .................... A61F 9/00804 219/121.8 |
| 6,238,385 B1 | 5/2001 | Harino et al. |
| 6,267,756 B1 | 7/2001 | Feuerstein et al. |
| D447,567 S | 9/2001 | Murphy et al. |
| 6,328,733 B1 | 12/2001 | Trost |
| RE37,504 E * | 1/2002 | Lin ..................... A61F 9/008 128/898 |
| 6,347,244 B1 | 2/2002 | Dubnack |
| 6,494,878 B1 | 12/2002 | Pawlowski et al. |
| 6,585,725 B1 * | 7/2003 | Mukai .................. A61B 18/203 606/10 |
| 6,652,511 B1 | 11/2003 | Tomita |
| 6,789,900 B2 | 9/2004 | Van de Velde |
| 6,904,305 B2 | 6/2005 | Tsekos |
| 6,913,603 B2 | 7/2005 | Knopp et al. |
| 7,146,983 B1 | 12/2006 | Hohla et al. |
| 2003/0231827 A1 | 12/2003 | Andersen et al. |
| 2004/0143245 A1 * | 7/2004 | Gray ................... A61F 9/00804 606/5 |
| 2005/0094262 A1 * | 5/2005 | Spediacci .......... G02B 21/0012 359/380 |
| 2006/0100677 A1 | 5/2006 | Blumenkranz et al. |

FOREIGN PATENT DOCUMENTS

| | | | |
|---|---|---|---|
| WO | 1997/017011 A1 | 5/1997 | |
| WO | WO 2004007022 A1 * | 1/2004 | ........... A61B 18/203 |
| WO | 2005/065116 A2 | 7/2005 | |

OTHER PUBLICATIONS

International Search Report and Written Opinion received for PCT Patent Application No. PCT/US2006/036782, dated Apr. 28, 2009, 6 pages.
Extended European Search Report received for European Patent Application No. 06815079.6, dated Sep. 10, 2010, 6 pages.
Barrett et al., "Computer-Aided Retinal Photocoagulation System", Journal of Biomedical Optics, vol. 1, No. 1, Jan. 1996, pp. 83-91.
Barrett et al., "Digital Imaging-Based Retinal Photocoagulation System", SPIE, vol. 2971, Feb. 8, 1997, pp. 118-128.
Markow et al., "An Automated Laser System for Eye Surgery", IEEE Engineering in Medicine and Biology Magazine, Dec. 1989, pp. 24-29.
Naess et al., "Computer-Assisted Laser Photocoagulation of the Retina—A Hybrid Tracking Approach", Journal of Biomedical Optics, vol. 7, No. 2, Apr. 2002, pp. 179-189.
Van De Velde, F. J., "Role of the Scanning Laser Ophthalmoscope in Photodynamic Therapy of Macular Disease", Ophthalmic Technologies X; Proceedings of SPIE, vol. 3908, 2000, pp. 190-201.
Wright et al., "Hybrid Approach to Retinal Tracking and Laser Aiming for Photocoagulation", Journal of Biomedical Optics, vol. 2, No. 2, Apr. 1997, pp. 195-203.
Wright et al., "Initial In Vivo Results of a Hybrid Retinal Photocoagulation System", Journal of Biomedical Optics, vol. 5, No. 1, Jan. 2000, pp. 56-61.

* cited by examiner

SYSTEM AND METHOD FOR GENERATING TREATMENT PATTERNS

This application is a continuation of U.S. Non-provisional application Ser. No. 11/523,392, filed Sep. 18, 2006, which claims the benefit of U.S. Provisional Application No. 60/718,762, filed Sep. 19, 2005, and of U.S. Provisional Application No. 60/758,169, filed Jan. 10, 2006. The content of these applications are hereby incorporated by reference.

FIELD OF THE INVENTION

The present invention relates to retinal photocoagulation, and more particularly to a system and method for patterned optical ophthalmic treatment.

BACKGROUND OF THE INVENTION

Presently, conditions such as diabetic retinopathy and age-related macular degeneration are subject to photocoagulative treatment with visible laser light. While this type of visible laser light treatment halts the progress of the underlying disease, it can be problematic. For example, because the treatment entails exposing the eye to visible laser light for a long period of time (typically on the order of 100 ms), damage can be caused to the patient's sensory retina from the heat that is generated. During the treatment, heat is generated predominantly in the retinal pigmented epithelium (RPE), which is the melanin containing layer of the retina directly beneath the photoreceptors of the sensory retina. Although light is absorbed in the RPE, this type of treatment irreversibly damages the overlying sensory retina and negatively affects the patient's vision.

Another problem is that some treatments require the application of a large number of laser doses to the retina, which can be tedious and time consuming. Such treatments call for the application of each dose in the form of a laser beam spot applied to the target tissue for a predetermined amount of time. The physician is responsible for ensuring that each laser beam spot is properly positioned away from sensitive areas of the eye that could result in permanent damage. Since some treatments can require hundreds of laser beam spots to evenly treat the target tissue, the overall treatment time can be quite long and require great physician skill to ensure an even and adequate treatment of the entire target tissue area.

To reduce the treatment time needed for retinal photocoagulation, a system and method has been proposed for applying multiple laser spots automatically in the form of a pattern of spots, so that an area of target tissue is efficiently treated by multiple spots pre-positioned on the tissue in the form of the pattern. See for example U.S. Patent Publication US2006/0100677. However, rapid delivery of multiple beam spots in patterns raises new issues. For example, localized heating can occur with the rapid and consecutive delivery of adjacent beam spots within a pattern. Moreover, variations in the patterns are needed to provide better exclusion zone and beam spot density control (both for even density and variable density), as well as better system control through a graphic user interface.

SUMMARY OF THE INVENTION

The present invention solves the aforementioned problems by providing a system and method of automatic projection of spot patterns onto the target tissue. More particularly, a photomedical system for treating target tissue includes a light source for generating a beam of light, a scanner assembly for translating the beam to form a pattern of spots of the light, a focusing element for focusing the pattern of spots on the target tissue, a controller for controlling the scanner assembly, and a graphic user interface connected to the controller that includes a display for displaying a configuration of the pattern of spots and for displaying a plurality of different pattern configurations to choose from for the pattern of spots in response to an activation of the display.

A method of treating target tissue includes selecting a pattern of spots from a plurality of different pattern configurations displayed on a display of a graphic user interface by activating the display, generating a beam of light, translating the beam to form the selected pattern of spots of the light, and focusing the pattern of spots of the light on the target tissue.

Other objects and features of the present invention will become apparent by a review of the specification, claims and appended figures.

BRIEF DESCRIPTION OF THE DRAWINGS

FIG. 18 is a front view of the graphic user interface screen displaying multiple possible pattern configurations from which to choose from.

DETAILED DESCRIPTION OF THE PREFERRED EMBODIMENTS

Figure 1:
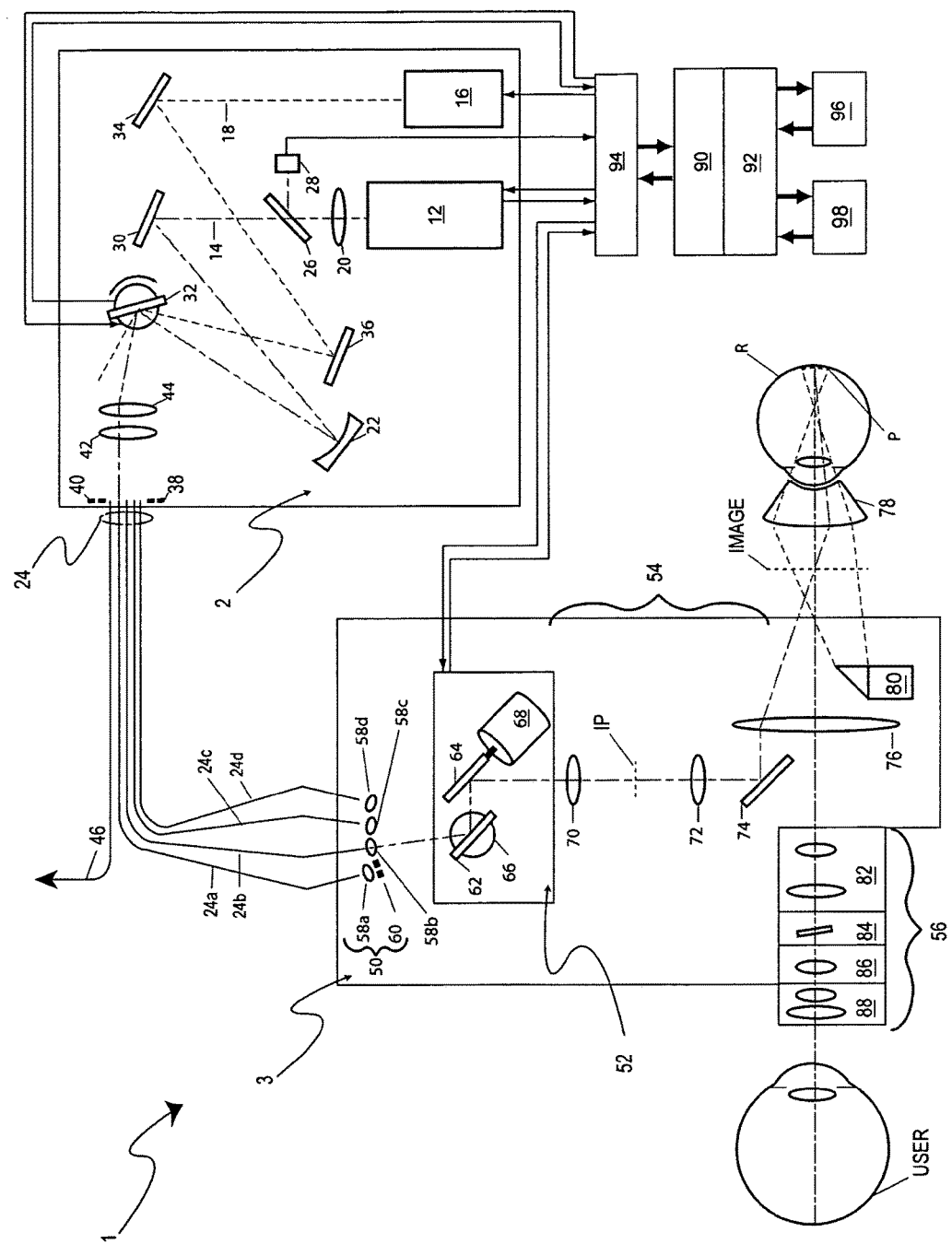
FIG. 1 is a schematic diagram of the scanning coagulation system.

The present invention is a system and method for generating patterns P of aiming and treatment light on target eye tissue (e.g. the retina) of a patient's eye. FIG. 1 depicts an ophthalmic slit lamp based scanning photocoagulator 1, which is a non-limiting example of a photocoagulation system for creating and projecting aiming and/or treatment patterns of spots onto a patient's retina R. System 1 includes a light source assembly 2 and a slit lamp assembly 3.

The light source assembly 2 includes a treatment light source 12 for generating an optical beam of treatment light 14, and an aiming light source 16 for generating an optical beam of aiming light 18. Treatment beam 14 from treatment light source 12 is first conditioned by lens 20, which is used in conjunction with a curved mirror 22 to prepare treatment beam 14 for input into an optical fiber bundle 24. After encountering lens 20, treatment beam 14 is sampled by partially reflecting mirror 26. The light reflected from mirror 26 is used as an input for a photodiode 28 that monitors the output power of treatment beam 14, assuring that the light source 12 is operating at the desired power. A mirror 30 is used to steer treatment beam 14 onto mirror 22, which in turn directs treatment beam 14 onto moving mirror 32. Aiming beam 18 from aiming light source 16 is directed onto moving mirror 32 via mirrors 34 and 36.

Moving mirror 32 is preferably mounted on a galvanometric scanner (but could also be moved by piezo actuators or other well know optic moving devices), and moves to selectively direct treatment and aiming beams 14, 18 to one of the optical fibers 24a, 24b, 24c, 24d of optical fiber bundle 24 at any given time, where lenses 42, 44 focus the treatment and aiming beams 14, 18 into the selected optical fiber(s). Preferably, moving mirror 32 is spaced one focal length away from lens 20 to provide for a telecentric scan condition (thus allowing for the injection of treatment beam 14 into all the optical fibers 24a-24d on parallel paths, which preserves the launch numerical aperture across the optical fiber bundle 24). Adjacent to the optical fibers 24a-24d are beam dumps 38, 40, which provide convenient locations to "park" the treatment beam 14. Optical fibers 24a-24d are used to deliver the treatment and aiming beams 14, 18 from the light source assembly 2 to the slit lamp assembly 3. An additional optical fiber 46 may be used to direct the treatment and/or aiming beams 14, 18 to the patient via other means such as an endoprobe or laser indirect ophthalmoscope (not shown).

Slit lamp assembly 3 includes an optical fiber input 50 (for receiving optical fibers 24a-24d), a scanner assembly 52, a delivery assembly 54, and a binocular viewing assembly 56. The optical fiber input 50 preferably includes a unique optical conditioning system for each of the optical fibers 24a-24d, so that each optical fiber can produce a specific (and preferably unique) spot size at the image plane IP of the slit lamp assembly 3. For example, light from optical fiber 24a first encounters a lens 58a that collimates the light, followed by an aperture 60 that serves to reduce the effective numerical aperture by obscuring all but the central portion of the light beam. Light from optical fibers 24b through 24d first encounter lenses 58b through 58d, respectively. Lenses 58b-58d are preferably configured to create different spot sizes at the image plane IP, and subsequently at the target tissue (retina R). In the illustrated example, optical fibers 24a and 24b have the same core diameter, but are made to create different spot sizes by using different lenses 58a and 58b. Optical fibers 24c and 24d have different core diameters. It is preferable (but not necessary) that all optical fibers deliver light with the same numerical aperture. Therefore, to keep the operating numerical apertures identical for these different channels, aperture 60 is used to counteract the change in optical power of lens 58a relative to lenses 58b, 58c, 58d.

The optical output of each optical fiber 24a-24d after conditioning by the associated optical systems (e.g. lenses 58a-58d, aperture 60, etc.) is directed to the scanner assembly 52, which includes two movable mirrors 62, 64 mounted to two galvanometers 66, 68 (although any well known optic moving device such as piezo actuators could be used). Mirrors 62, 64 are configured to rotate in two orthogonal axes to scan (i.e. translate) the incoming light to form any desired pattern P. Mirror 62 may be rotated to redirect the light from any given one of the fibers 24a-24d into the remainder of slit lamp assembly 3, thus acting to "select" the output from that optical fiber while prohibiting any light from the other optical fibers to continue through the entire slit lamp assembly 3. Because the output ends of optical fibers 24a-24d are not coincident, mirror 62 must be rotated into position to intercept the light from the desired optical fiber and transmit that light to mirror 64, which can further move the light in an orthogonal axis. This configuration has the added benefit of preventing any stray light that may be delivered by the non-selected optical fibers from exiting the system. In FIG. 1, optical fiber 24b is shown as the selected fiber, where the output of this fiber is scanned by mirrors 62, 64 to create a scanned pattern of light that travels through the rest of the system.

The scanned pattern of light P (which originates from treatment light source 12 and/or aiming light source 14) leaving the scanner assembly 52 passes through the delivery assembly 54, which includes lens 70 (for creating the intermediate scanned pattern at image plane IP), lens 72 (for conditioning the light pattern for focusing into the eye), mirror 74 (for directing the light pattern toward the target eye tissue), lens 76 (preferably an infinity-corrected microscope objective lens) and lens 78 (preferably a contact lens that provides final focusing of the pattern of light P onto the target eye tissue such as the retina R). Illumination source 80 (such as a halogen light bulb) is used to illuminate the target eye tissue R so that the physician can visualize the target eye tissue.

The user (i.e. physician) views the target eye tissue R directly via the binocular viewing assembly 56, which includes magnification optics 82 (e.g. one or more lenses used to magnify the image of the target eye tissue, and preferably in an adjustable manner), an eye safety filter 84 (which prevents potentially harmful levels of light from reaching the user's eye, and which may be color-balanced to provide for a photopically neutral transmission), optics 86, and eyepieces 88.

Pattern P of light is ultimately created on the retina of a patient R using optical beams 14, 18 from treatment light source 12 and aiming light source 16 under the control of control electronics 90 and central processing unit (CPU) 92. Control electronics 90 (e.g. field programmable gate array, etc.) and CPU 92 (e.g. a dedicated microprocessor, a standalone computer, etc.) are connected to various components of the system by an input/output device 94 for monitoring and/or controlling those components. For example, control electronics 90 and/or CPU 92 monitor photodiode 28 (to ensure treatment beam 14 is generated at the desired power level), operate the light sources 12, 16 (turn on/off, set power output level, etc.), operate mirror 32 (to select which optical fiber will be used for treatment and/or aiming beams 14, 18), and control the orientations of galvanometric scanners 66, 68 to produce the desired pattern P on the target eye tissue. CPU 92 preferably serves to support control electronics 90, and serves as input for a graphical user interface (GUI) 96 and an alternate user input device 98. GUI 96 allows the user to command various aspects of the system, such as the delivered spot size and pattern, pulse duration and optical power output from treatment light source 12 and aiming light source 16. In addition to the user physically moving slit lamp assembly 3 for gross alignment, the ultimate fine alignment of the light pattern P on the target tissue may be further controlled by use of the input device 98 (which can be a joystick, a touchpad, etc.), which causes mirrors 62, 64 alter their rotations when scanning the light beam thus translating the entire pattern P on the target tissue. This approach yields very fine control of the disposition of the scanned beam. Additional input devices 98 can be included, such as knobs to adjust the output power of the light sources 12, 16, a footswitch or other type of activation device to activate the application of the aiming pattern and/or treatment pattern, etc. The ultimate disposition of the optical output of light sources 12, 16 is intended to be the pattern P contained in the patient's retina R.

Figure 2:
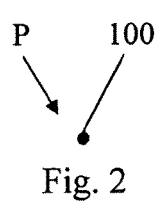
FIG. 2 is a diagram of a pattern P of a single spot.
Figure 3A:
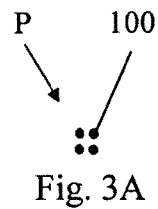
FIGS. 3A-3G are diagrams of symmetrical patterns P of spots.
Figure 3B:
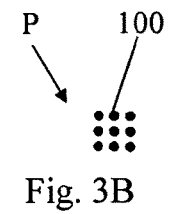
Figure 3C:
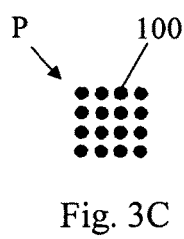
Figure 3D:
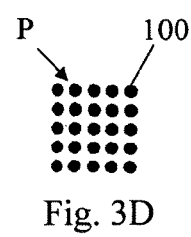
Figure 3E:
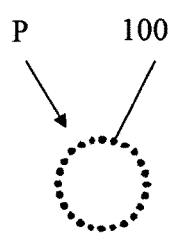
Figure 3F:
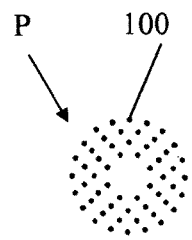
Figure 3G:
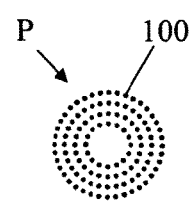
Figure 4A:
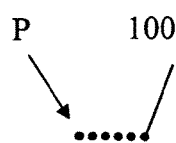
FIGS. 4A-4F are diagrams of non-symmetrical patterns P of spots.
Figure 4B:
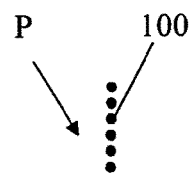
Figure 4C:
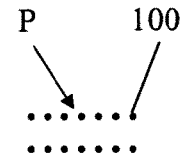
Figure 4D:
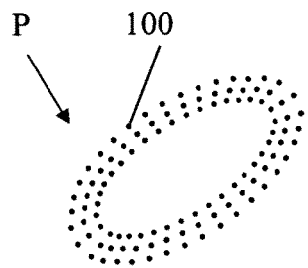
Figure 4E:
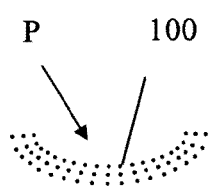
Figure 4F:
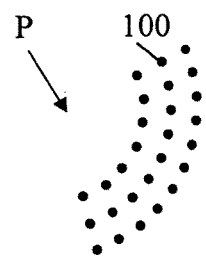
Figure 5A:
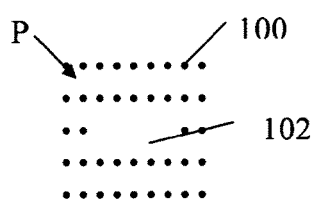
FIGS. 5A-5B are diagrams of patterns P of spots with fully enclosed exclusion zones.
Figure 5B:
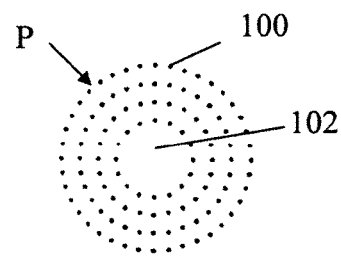
Figure 6A:
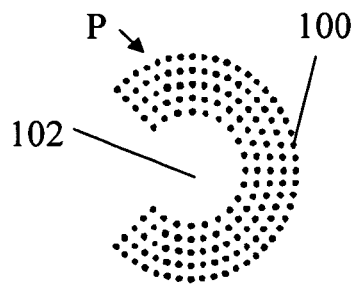
FIGS. 6A-6B are diagrams of patterns P of spots with partially open exclusion zones.
Figure 6B:
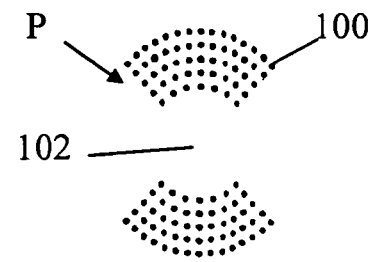

The most basic types of patterns P are those formed of discrete, uniformly sized and uniformly spaced fixed spots. The user can use GUI 96 to select, modify, and/or define a number of pattern variables, such as: spot size, spot spacing (i.e. spot density), total number of spots, pattern size and shape, power level, pulse duration, etc. In response, the CPU 92 and control electronics 90 control the treatment light source 12 (assuming it is a pulsed light source) or additionally a shuttering mechanism (not shown) somewhere along the beam 14 to create pulsed treatment light. Mirrors 62, 64 move between pulses to direct each pulse to a discrete location to form a stationary spot. FIG. 2 shows a pattern P having a single spot 100. FIGS. 3A-3G show fully symmetrical (i.e. symmetrical in both the vertical and horizontal axes) square or circular patterns P of spots 100. FIGS. 4A-4D show non-symmetrical patterns P of spots 100 such as lines, rectangles and ellipses. FIGS. 5A-5B show patterns P of spots 100 with completely enclosed exclusion zones 102, which are zones within the pattern P that are free of spots 100. FIGS. 6A-6B show patterns P of spots 100 with partially open exclusion zones 102, where the exclusion zone 102 is not completely surrounded by the spots 100. Different patterns are ideal for different treatments. For example, a single spot pattern is ideal for titrating the power for treatment, performing touchups to space between pattern spots, and sealing individual micro-aneurysms. Rectangle, square and line patterns are ideal for PRP (panretinal photocoagulation). Elliptical and circular patterns are ideal for treating the macula, and sealing tears. Arc patterns (i.e. circular or elliptical wedge patterns but without a radially center portion as shown in FIG. 4F) are ideal for partially surrounding and treating a tear, as well as for PRP treatment for periphery and lattice degeneration. Patterns with enclosed exclusion zones are ideal for treating around sensitive areas such as the fovea where it is important that the sensitive area not receive any treatment light. Patterns with partially open exclusion zones are ideal for treating sensitive areas that are connected to other sensitive areas, such as avoiding treatment of both the fovea and the optic nerve that extends from the fovea—see especially pattern P in FIG. 6A).

Figure 7:
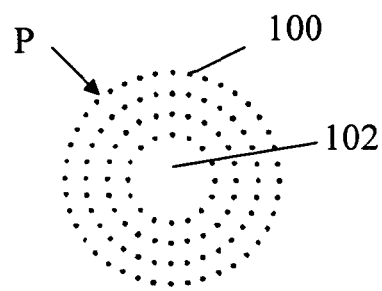
FIG. 7 is a diagram of a circular pattern P of spots having a generally uniform spot density.

FIG. 7 illustrates a circular pattern P with a substantially uniform spot density. With rectangular shaped patterns, uniform spot density over the entire pattern P is easily achieved by making the rows and columns equally spaced apart and spots 100 all the same size. However, with a circular pattern, uniformity is not easily achieved. Forming concentric circles of spots with the same number of spots in each circle will result in a reduced spot density as the radius increases. Therefore, the following criteria has been developed to maximize the uniformity of the spot density of a circular pattern P of spots 100 (where the following calculations are preferably performed by the CPU 92):

1) Spots 100 are positioned in N circles of different radii all concentrically positioned around a single central point.
2) The diameter D(n) of the nth circle of pattern P (where n=1, 2, ... N, and n=1 is the circle closest to the center) is:

$$D(n) = EZ + S_D + (n-1) \times S_D(1 + \text{Round}(DF)) \qquad (1)$$

where EZ is the diameter of the desired exclusion zone if any (i.e. desired diameter of most inner circle), $S_D$ is the diameter of the spots, and Round(DF) is the density factor DF rounded (up or down) to the nearest whole number. The density factor DF is a number preferably selected or adjusted by the user via the system GUI 96. Typical density factors for eye surgery can be in the low single digits. If no exclusion zone is desired, then n=2, 3, ... N, and n=2 is the circle closest to the center
3) The number of spots 100 in the nth circle of pattern P is:

$$\text{Number}(n) = 8 \times \text{Round}\left[\pi \times D(n) \times \frac{1}{8} \times \frac{1}{S_D} \times \frac{1}{DF}\right] \qquad (2)$$

where Round here is rounding (up or down) to the nearest whole number.
4) If there is no exclusion zone EZ, then n=2, 3 ... N, with n=2 corresponding to the circle closest to the center.

These same equations can be utilized to form constant density concentric arcs of equal angular extent A along N concentric circles (e.g. see FIGS. 4F, 6A, 6B). For calculating the diameter of the circle on which the arcs lie, equation (1) is the same, where A is the angular extent of the arcs and is between 0 and $2\pi$. The number of spots in each concentric arc is (i.e. equation (2) becomes):

$$\text{Number}(n) = 8 \times \text{Round}\left[\pi \times D(n) \times \frac{1}{8} \times \frac{1}{S_D} \times \frac{1}{DF} \times \frac{A}{2\pi}\right] \qquad (3)$$

Figure 8:
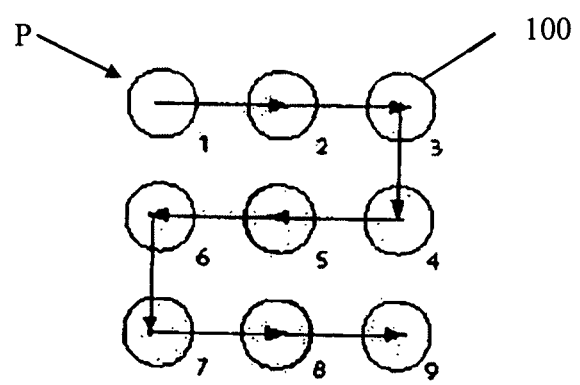
FIG. 8 is a diagram illustrating the scanning order of a pattern P of spots with adjacent spots scanned consecutively.
Figure 9A:
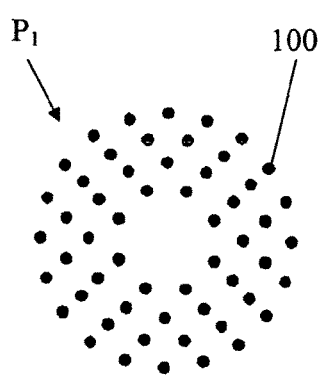
FIGS. 9A and 9B are diagrams illustrating adjacent spots from a single pattern P separated into two different spot patterns.
Figure 9B:
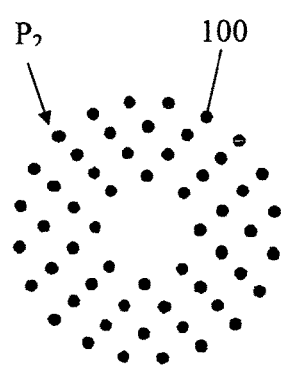
Figure 9C:
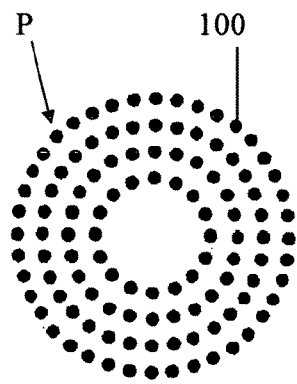
FIG. 9C is a diagram illustrating the pattern P of spots resulting from the combination of patterns in FIGS. 9A and 9B.

The most straight forward technique for scanning spots 100 in a pattern P is sequentially where adjacent spots are scanned consecutively from one end of the pattern to the other to minimize the amount of scanning mirror movement between spots (as illustrated in FIG. 8). However, exposing two adjacent spots consecutively (one just after the other) may result in undesirable localized heating. Thus, interlaced patterns can be used to minimize localized heating. Interlaced patterns are patterns that overlap each other in an alternating manner, so that the patterns themselves overlap each other, but the spots of one pattern do not overlap spots of the other pattern (i.e. spots of one pattern are positioned among the spots of the other in an alternating or intermixed manner). FIGS. 9A and 9B represent how a pattern P (illustrated in FIG. 9C) can be split up into two separate patterns $P_1$ and $P_2$ of alternating spots, so that spots immediately adjacent to each other in the pattern P are scanned onto the target tissue in two separate patterns (and thus more separated in time). In the particular example of FIGS. 9A-9C, pattern $P_1$ represents half of the total spots in pattern P, and pattern $P_2$ represents the same pattern as pattern $P_1$ except it is rotated by a predetermined angle (e.g. 11.25 degrees). Thus pattern $P_1$ of FIG. 9A is scanned in its entirety, then pattern $P_2$ of FIG. 9B is scanned in its entirety in an interlaced fashion relative to pattern $P_1$, thus resulting in pattern P of FIG. 9C that induces less localized heating during its scan onto the target tissue.

Figure 10A:
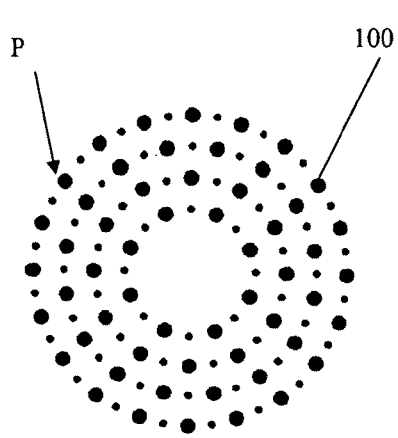
FIGS. 10A-10B are diagrams of a pattern P of spots with adjacent spots having different sizes.
Figure 10B:
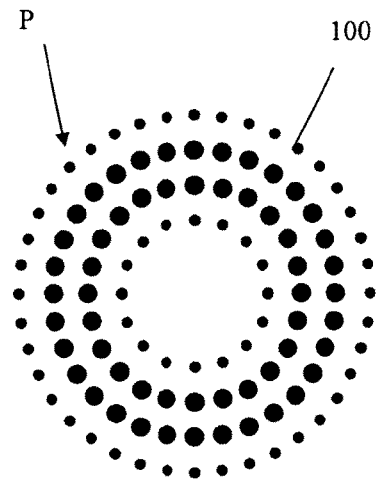

FIG. 10A illustrates a variation of the interlacing of the two patterns $P_1$ and $P_2$ to result in pattern P. In this configuration, the size of spots 100 forming pattern $P_2$ is smaller than that of the spots 100 forming pattern $P_1$. Thus, in the combined pattern P, adjacent spots have different sizes. This has the advantage of preserving more of the untreated retina and maintaining open space for subsequent follow-up treatment(s) (i.e. variable dosing). FIG. 10B is a variation on FIG. 10A, in which the spot size is consistent within the same ring, but spot sizes from one ring to the next can vary.

Figure 11A:
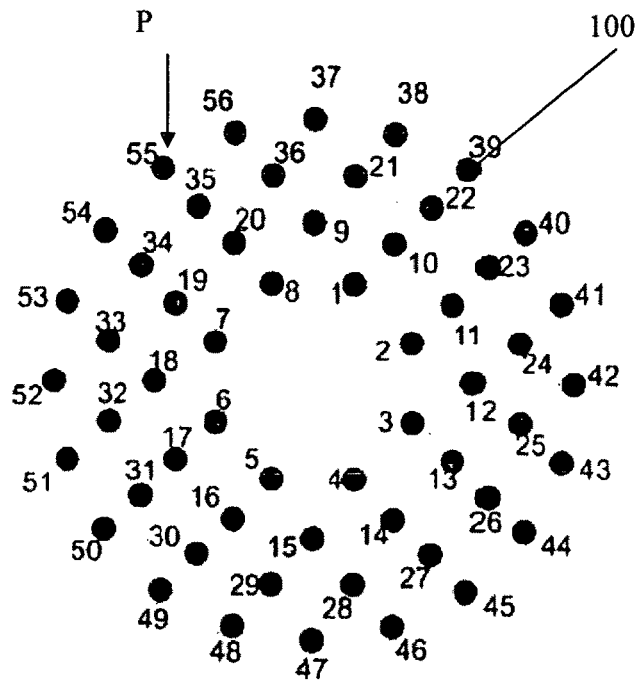
FIGS. 11A and 11B are diagrams illustrating two different scanning orders of a round pattern P of spots.
Figure 11B:
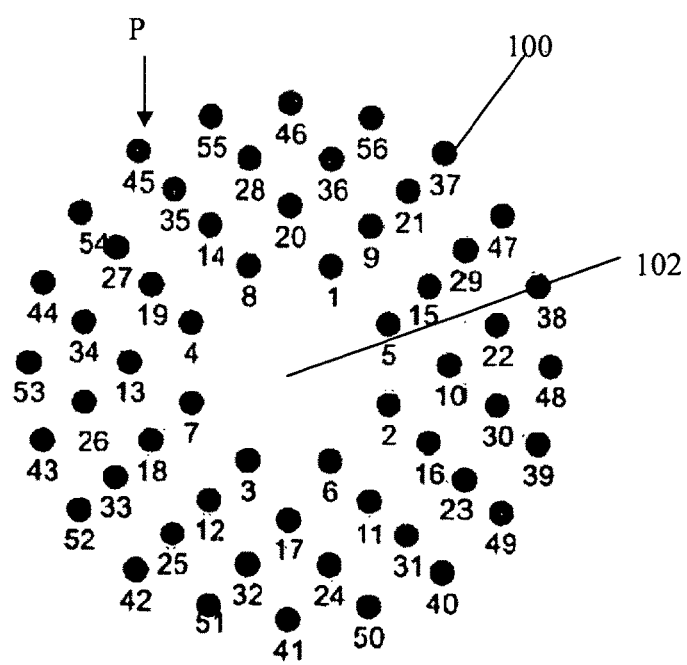

FIGS. 11A-11B illustrate how varying the spot sequencing can be used to balance control of localized heating with other considerations. In FIG. 11A, the sequence in which each spot is scanned is numbered. Thus, the first eight pulses are used to consecutively scan the eight spots that form the innermost circle. Then, the next most innermost circle is consecutively scanned, and so on. Each circle is scanned in a single direction with adjacent spots being scanned in consecutive order. The advantage of this pattern sequence is that the innermost circle closest to the exclusion zone 102 is scanned first, so that if the patient's eye moves later on while the pattern is still being scanned, the beam at that point in the treatment will be further away from the sensitive eye tissue in the exclusion zone and thus will minimize the risk of inadvertent exposure to this tissue (e.g. the fovea). It should be noted that this spot sequence results in adjacent spots in each circle being scanned consecutively, which may result in undesirable localized heating. In FIG. 11B, the spot sequence is modified so that each circle is scanned one at a time starting with the innermost circle, but within each circle adjacent spots are not scanned consecutively (i.e. adjacent pulses in the beam are not used to scan adjacent spots in the final pattern). This can entail either a random ordering, or a more orderly sequence such as scanning every other spot as the beam traverses around the circle (as shown in FIG. 11B).

Figure 12A:
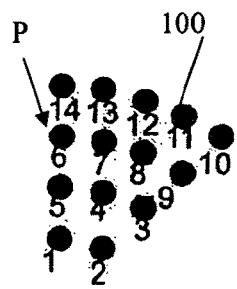
FIGS. 12A and 12B are diagrams illustrating two different scanning orders of a wedge shaped pattern P of spots.
Figure 12B:
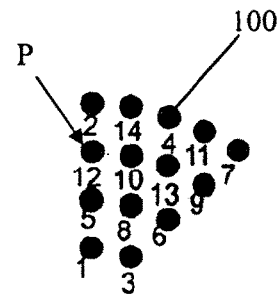
Figure 13A:
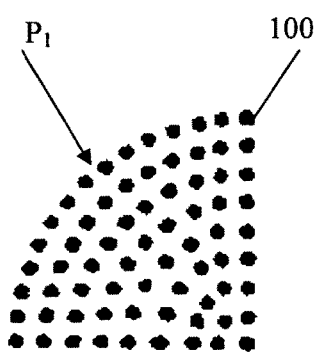
FIGS. 13A and 13D are diagrams illustrating four separately scanned sub-patterns that together form scanned pattern P.
Figure 13B:
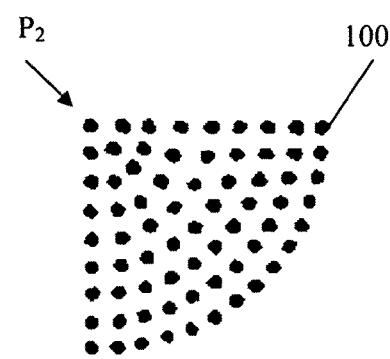
Figure 13C:
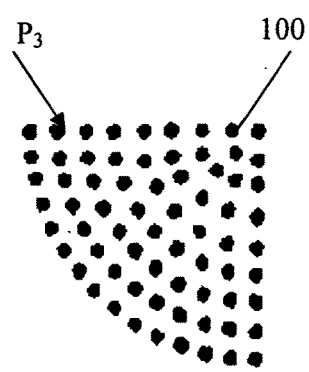
Figure 13D:
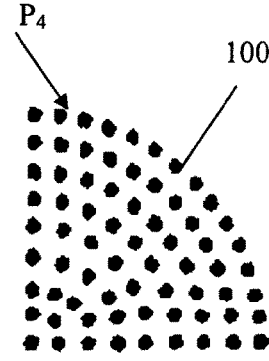

FIGS. 12A and 12B show pulse sequencing similar to that of FIGS. 11A and 11B, except as applied to a wedge shaped pattern P. Specifically, in FIG. 12A, arcs of different radii are scanned one arc at a time, in order, starting from the innermost circle. In FIG. 12B, the spots 100 of the wedge shaped pattern P are scanned randomly both within as well as among the different arcs.

FIGS. 13A-13D show how a larger pattern P can be broken up into sub-patterns. Specifically, instead of scanning the entire pattern P (in this example a circular pattern), it may be preferable to break up the pattern P into sub-patterns (in this example wedge-shaped quadrants), and scan each sub-pattern $P_1$, $P_2$, $P_3$, $P_4$ in its entirety before moving on to the next sub-pattern. Within each sub-pattern, the spots may be scanned out of order to minimize localized heating as discussed above. The advantage of this technique is that if the scanning were interrupted during one sub-pattern (e.g. due to excessive eye movement), the system can better recover by simply moving on to the next sub-pattern. Trying to resume a partially completed scan of a pattern may not be feasible in some applications once registration between the scanner and the target tissue is lost. In other words, it is easier to register the location of an entire sub-pattern and continue rather than try to register the location of the remaining spots within a partially completed scanned pattern. By scanning the spots using sub-patterns to form an overall pattern P, and each sub-pattern is scanned without scanning adjacent spots consecutively, there is a good balance between small pattern local working areas and avoidance of excessive localized heating.

Figure 14A:
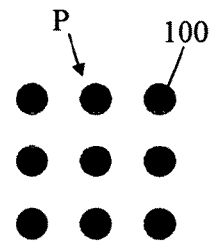
FIGS. 14A-14D are diagrams illustrating aiming patterns that either enclose the area in which the treatment pattern P of spots of will be positioned or identify the center and outer extent of the treatment pattern P.
Figure 14B:
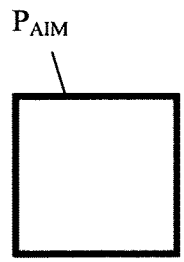
Figure 14C:
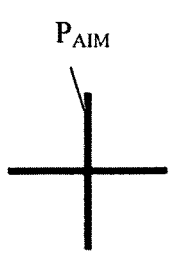
Figure 14D:
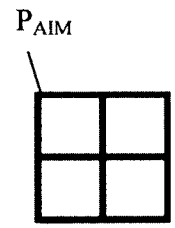
Figure 15A:
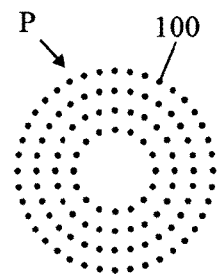
FIGS. 15A-15D are diagrams illustrating aiming patterns that either enclose the area in which the treatment pattern P of spots of will be positioned or identify the center and outer extent of the treatment pattern P.
Figure 15B:
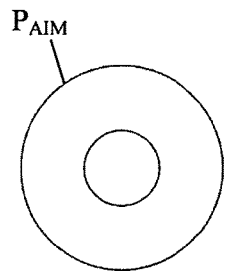
Figure 15C:
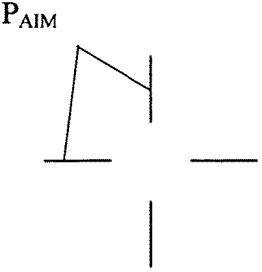
Figure 15D:
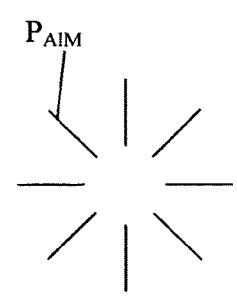

There are various relationships that the aiming beam can take relative to the treatment beam. For example, the aiming light can be projected onto the target tissue in a pattern that generally matches that of the treatment light (i.e. the system projects a pattern P of spots with the aiming light, followed by the projection of the pattern P of spots with the treatment light overlapping the positions of the spots projected by the aiming light). In this manner, the physician can align the pattern P of treatment light spots knowing they will be positioned where the pattern P of alignment light spots are seen on the target tissue. Alternately, the aiming light can be scanned in a pattern $P_{AIM}$ of enclosed shape (e.g. circle, rectangle, ellipse, etc.), where the treatment light pattern P of spots will be inside that enclosed shape (i.e. the pattern $P_{AIM}$ of aiming light outlines the target tissue that will receive the treatment light pattern P). Thus, $P_{AIM}$ of FIG. 14B outlines the pattern P of FIG. 14A, and $P_{AIM}$ of FIG. 15B outlines the pattern P of FIG. 15A. In yet another example, the alignment pattern $P_{AIM}$ can identify the center of the treatment light pattern P of spots, and possibly indicate the extent of the treatment light pattern P of spots (e.g. alignment pattern $P_{AIM}$ is cross hairs showing the center of the treatment light pattern P, with the outer ends of the cross hairs indicating the outer perimeter of the treatment light pattern P. Thus, $P_{AIM}$ of FIGS. 14C and 14D identify the center and extent of the pattern P of FIG. 14A, and $P_{AIM}$ of FIGS. 15C and 15D identify the center and extent of the pattern P of FIG. 15A.

Figure 16:
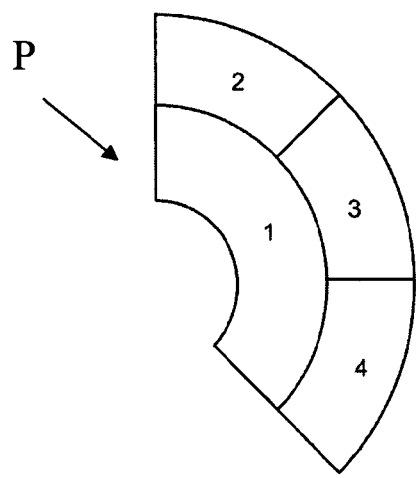
FIG. 16 is a diagram illustrating automatic generation of arc patterns.

FIG. 16 illustrates how the system can automatically generate pattern sizes that exceed the scan size capabilities of the system. In FIG. 16, the desired pattern P is in the shape of a circular arc, with four sub-arc patterns 1-4. The system can be set to allow the user to define the innermost sub-arc pattern 1 as a first scan, where the system will proceed to scan sub-arc pattern 1, and then automatically identify and scan in sequential order sub-arc patterns 2, 3, 4 which are disposed radially outwardly from the sub-arc pattern 1. With this configuration, a user can define an arc shaped pattern that approaches the scan limits of the system, and the system will automatically scan additional sub-patterns disposed radially outwardly from the pattern identified by the user.

Figure 17:
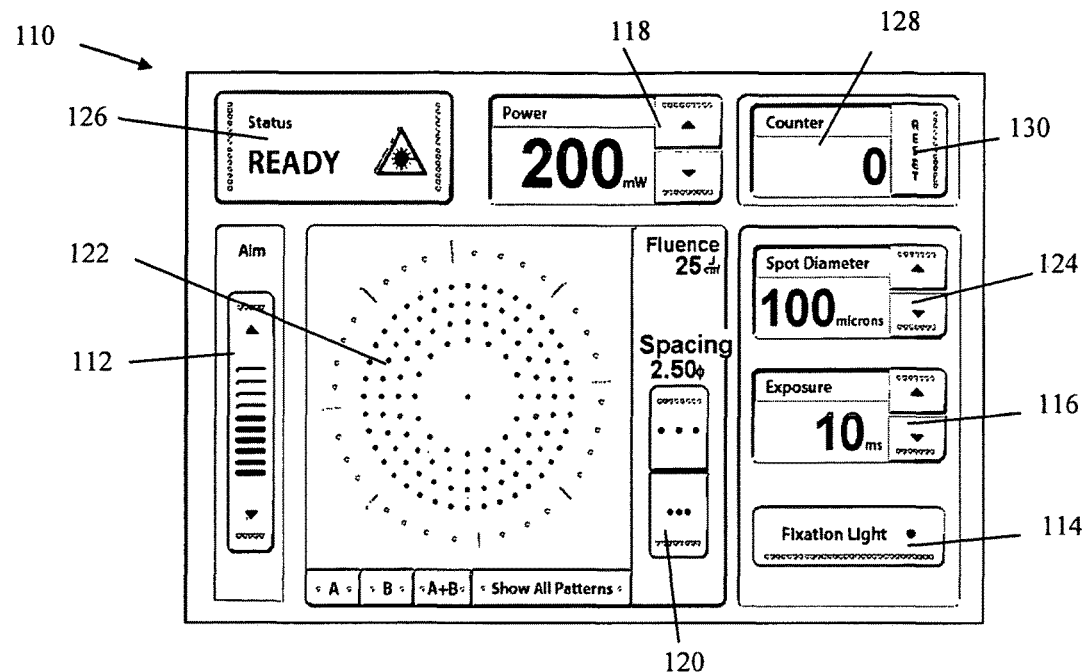
FIG. 17 is a front view of a graphic user interface screen for operating the photocoagulation system.
Figure 18:
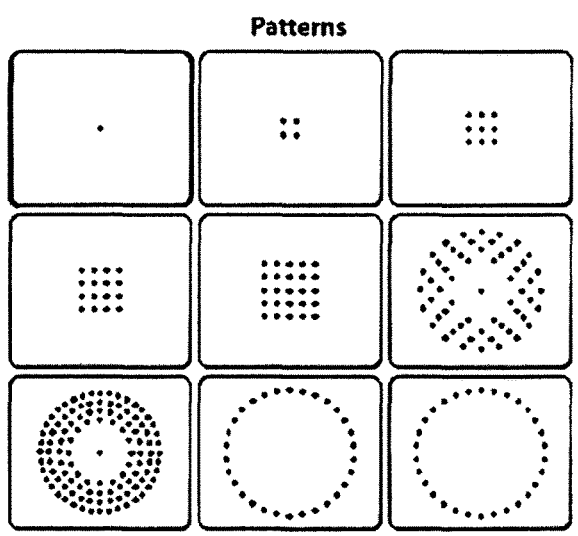

FIG. 17 illustrates an exemplary graphic user interface (GUI) 96 for selecting and implementing the above described photocoagulation patterns. The illustrated GUI 96 comprises a touch screen display 110, which defines soft keys on the screen can be used to change the operating conditions of the system. For example, the display 110 defines soft keys for adjusting aim beam power 112, fixation light power 114, exposure time 116, treatment power 118, spot density 120, pattern 122, and spot diameter 124. Touching these soft keys allows the user to adjust the selected parameter(s). Some soft keys are in the form of up/down arrows, which allow the user to directly adjust the numeric value. Other soft keys provide multiple options (e.g. spot density 120) from which the user can select the desired option. Still other soft keys illustrate an operating parameter, and when activated open new menus from which to manipulate that operating parameter (e.g. the pattern soft key 122 illustrates the configuration of the selected pattern such as spot spacing and pattern shape and layout, and when activated such as being touched opens a menu for selecting from a plurality of predefined patterns as illustrated in FIG. 18, or for defining a new pattern; the spot diameter soft key 124 indicates the size of the spots and when touched opens a menu for adjusting the spot size). Status indicators are also provided on display 110 (e.g. status indicator 126 indicates whether the system is in a standby mode, an aiming light mode, or a treatment light mode; counter indicator 128 keeps track of the number of treatment applications and can be reset by touching the reset soft key 130). Soft keys can also be tailored to the specific data being input. For example, by dragging the user's finger around pattern soft key 122 allows the user to select how many quadrants, octants, etc. that will be included in a circular pattern (e.g. dragging around the pattern key 122 for approximately 310 degrees will select a pattern with seven octants—i.e. one octant will be left out of an otherwise complete circular pattern).

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

It is to be understood that the present invention is not limited to the embodiment(s) described above and illustrated herein, but encompasses any and all variations falling within the scope of the appended claims. For example, while many of the patterns P described above and illustrated in the figures have a uniform spot density configuration, the present invention is not so limited. The spot density can be varied in the same pattern P in various ways. For example, the sizes and/or separation of spots 100 in one portion of the pattern P can be different than that in another portion of the same pattern P. Treatment density can also be varied in the same pattern P, by varying the power and/or pulse duration that form spots in one portion of the pattern P relative to the power and/or pulse duration that spots in another portion of pattern P. Pattern P can not only be formed of discrete stationary spots as described above, but also by one or more moving spots that form scanned lines or other scanned images. The aiming light source (or another light source) can be used to project a fixation pattern on the eye along with the aiming pattern P and/or the treatment pattern P to give the patient a reference point to keep the eye still during treatment. The above system is ideal for, but not limited to, photocoagulation diagnosis/treatment. Lastly, as is apparent from the claims and specification, not all method steps necessarily need be performed in the exact order illustrated or claimed, but rather in any order that allows for the proper alignment and projection of the treatment pattern P.

What is claimed is:

1. A method of treating target tissue using a treatment system having a treatment light source, a scanner assembly, and control electronics, the method comprising:
    displaying, on a display, a graphical user interface having a plurality of pattern configurations;
    receiving a user selection of a pattern configuration of the plurality of pattern configurations;
    partitioning the pattern configuration into a first sub-pattern of spots and a second sub-pattern of spots, wherein the first sub-pattern of spots and the second sub-pattern of spots each include a plurality of concentric arcs or a plurality of rows and columns, and wherein the first sub-pattern of spots are interlaced with the second sub-pattern of spots to form the pattern configuration;
    in accordance with the user selection, initiating, at a first time, translation of a treatment beam of treatment light to form a portion of the first sub-pattern of the selected pattern configuration of spots on the target tissue;
    prior to completing formation of the first sub-pattern of the selected pattern configuration of spots on the target tissue, detecting an interruption event; and
    in accordance with detecting the interruption event:
        forgoing forming remaining spots of the first sub-pattern on the target tissue; and
        initiating, at a second time after the first time, translation of the treatment beam of treatment light to form the second sub-pattern of the selected pattern configuration of spots on the target tissue, wherein the treatment beam of treatment light is generated using the treatment light source and translated at the first and second times using the scanner assembly and the control electronics.

2. The method of claim 1, wherein displaying the graphical user interface comprises:
    displaying the graphical user interface on a touch sensitive screen.

3. The method of claim 1, wherein the spots in the first sub-pattern have a diameter that is greater than that of the spots in the second sub-pattern.

4. The method of claim 1, wherein the first and second sub-patterns of spots are the same.

5. The method of claim 4, wherein the first sub-pattern is positionally shifted relative to the second sub-pattern.

6. The method of claim 4, wherein the second sub-pattern is positionally rotated by a predetermined angle relative to the first sub-pattern.

7. The method of claim 1,
    wherein the portion of the first sub-pattern of spots is formed sequentially on the target tissue by initiating translation of the treatment beam of light at the first time,
    wherein the second sub-pattern of spots is formed sequentially on the target tissue by initiating translation of the treatment beam of light at the second time, and
    wherein adjacent spots in the overall selected pattern configuration are formed non-consecutively.

8. The method of claim 1, wherein the selected pattern configuration is substantially round in shape and has a substantially constant density of the spots.

9. The method of claim 1, wherein the spots in the selected pattern configuration are positioned in N concentric circles each concentric circle having a diameter D defined as:

$$D(n) = EZ + S_D + (n-1) \times S_D (1 + \text{Round}(DF))$$

wherein:
    $D(n)$ is the diameter of the nth concentric circle of the selected pattern configuration with n=1, 2, ... N,
    EZ is a diameter of an exclusion zone in a center of the selected pattern configuration, $S_D$ is a diameter of the spots, and Round (DF) is a density factor DF rounded up or down to the nearest whole number.

10. The method of claim 9, wherein each of the n=1, 2, ... N concentric circles includes a predetermined number (n) of the spots according to:

$$\text{Number}(n) = 8 \times \text{Round}\left[\pi \times D(n) \times \frac{1}{8} \times \frac{1}{S_D} \times \frac{1}{DF}\right]$$

wherein Round[ ] means rounding up or down to the nearest whole number.

11. The method of claim 1, wherein the spots in the selected pattern configuration are positioned in N concentric circles each concentric circle having a diameter D defined as:

$$D(n) = S_D + (n-1) \times S_D(1 + \text{Round}(DF))$$

wherein:

D(n) is the diameter of the nth concentric circle of the selected pattern configuration with n=2, 3, ... N, $S_D$ is a diameter of the spots, and Round(DF) is a density factor DF rounded up or down to the nearest whole number.

12. The method of claim 11, wherein each of the n=2, 3, ... N concentric circles includes a predetermined number (n) of the spots according to:

$$\text{Number}(n) = 8 \times \text{Round}\left[\pi \times D(n) \times \frac{1}{8} \times \frac{1}{S_D} \times \frac{1}{DF}\right]$$

wherein Round[ ] means rounding up or down to the nearest whole number.

13. The method of claim 1, wherein the spots in the selected pattern configuration are positioned in concentric arcs of equal angular extent A along N concentric circles each having a diameter D defined as:

$$D(n) = EZ + S_D + (n-1) \times S_D(1 + \text{Round}(DF))$$

wherein:

D(n) is the diameter of the nth concentric circle of the selected pattern configuration with n=1, 2, ... N, EZ is a diameter of an exclusion zone in a center of the selected pattern configuration, $S_D$ is a diameter of the spots, Round (DF) is a density factor DF rounded up or down to the nearest whole number, and A is the angular extent of the arcs and is between 0 and $2\pi$.

14. The method of claim 13, wherein each of the n=1, 2, ... N concentric arcs includes a predetermined number(n) of the snots according to:

$$\text{Number}(n) = 8 \times \text{Round}\left[\pi \times D(n) \times \frac{1}{8} \times \frac{1}{S_D} \times \frac{1}{DF} \times \frac{A}{2\pi}\right]$$

wherein Round[ ] means rounding up or down to the nearest whole number.

15. The method of claim 1, wherein the spots in the selected pattern configuration are positioned in concentric arcs of equal angular extent A along N concentric circles each having a diameter D defined as:

$$D(n) = S_D + (n-1) \times S_D(1 + \text{Round}(DF))$$

wherein:

D(n) is the diameter of the nth concentric circle of the selected pattern configuration with n=2, 3, ... N, $S_D$ is a diameter of the spots, Round(DF) is a density factor DF rounded up or down to the nearest whole number, and A is the angular extent of the arcs and is between 0 and 2n.

16. The method of claim 15, wherein each of the n=2, 3, ... N concentric arcs includes a predetermined number(n) of the spots according to:

$$\text{Number}(n) = 8 \times \text{Round}\left[\pi \times D(n) \times \frac{1}{8} \times \frac{1}{S_D} \times \frac{1}{DF} \times \frac{A}{2\pi}\right]$$

wherein Round[ ] means rounding up or down to the nearest whole number.

17. The method of claim 1, wherein the selected pattern configuration has a density of the spots that varies.

18. The method of claim 1, wherein the selected pattern configuration is an arc pattern, and wherein the method further comprises:

automatically initiating, at a third time after the second time, translation of the treatment beam of treatment light to form additional arc patterns radially outward from the arc pattern on the target tissue.

19. The method of claim 1, wherein the spots of the selected pattern configuration have varying diameters.

20. The method of claim 1, further comprising:

prior to the first time, generating an aiming beam of aiming light using an aiming light source of the treatment system;

translating the aiming beam to form an enclosed aiming pattern of the aiming light on the target tissue in which the selected pattern configuration of spots is to be confined.

21. The method of claim 1, further comprising:

prior to the first time, generating an aiming beam of aiming light using an aiming light source of the treatment system; and translating the aiming beam to form an aiming pattern of the aiming light on the target tissue that indicates a center position of the selected pattern configuration of spots.

22. The method of claim 21, wherein the aiming pattern further indicates an outer boundary in which the selected pattern configuration of spots is to be confined.

23. The method of claim 21, wherein the aiming pattern comprises two or more crossed lines.

24. The method of claim 1, wherein the selected pattern configuration of spots defines a partially enclosed exclusion zone on the target tissue in which the spots are not incident.

25. The method of claim 24, wherein the second subpattern of spots includes a plurality of sets of spots, wherein a first set of spots in the plurality of sets of spots is disposed closest to the exclusion zone relative to other sets of spots in the plurality of sets of spots, and wherein the first set of spots is scanned prior to the other sets of spots.

26. The method of claim 1, wherein the selected pattern configuration of spots comprises a plurality of arc patterns separated from each other.

27. The method of claim 1, further comprising:
prior to the first time, generating an aiming beam of aiming light using an aiming light source of the treatment system;
translating the aiming beam to form the selected pattern configuration of spots on the target tissue.

28. The method of claim 1, wherein the second sub-pattern of spots is scanned in a random ordering.

29. The method of claim 1, wherein the second sub-pattern of spots is scanned consecutively.

* * * * *

UNITED STATES PATENT AND TRADEMARK OFFICE
CERTIFICATE OF CORRECTION

PATENT NO. : 10,179,071 B2
APPLICATION NO. : 14/285205
DATED : January 15, 2019
INVENTOR(S) : David Haydn Mordaunt et al.

Page 1 of 1

It is certified that error appears in the above-identified patent and that said Letters Patent is hereby corrected as shown below:

In the Claims

In Column 11, Line 54, Claim 14, delete "snots" and insert -- spots --, therefor.

In Column 12, Line 9, Claim 15, delete "2n." and insert -- 2π. --, therefor.

Signed and Sealed this
Nineteenth Day of February, 2019

Andrei Iancu
*Director of the United States Patent and Trademark Office*